(12) United States Patent
Phillips et al.

(10) Patent No.: US 8,364,268 B2
(45) Date of Patent: *Jan. 29, 2013

(54) BI-DIRECTIONAL CONNECTOR ASSEMBLY FOR AN IMPLANTABLE MEDICAL DEVICE

(75) Inventors: William C. Phillips, Brooklyn Park, MN (US); Raymond F. McMullen, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/088,559

(22) Filed: Apr. 18, 2011

(65) Prior Publication Data

US 2011/0196448 A1  Aug. 11, 2011

Related U.S. Application Data

(63) Continuation of application No. 11/735,553, filed on Apr. 16, 2007, now Pat. No. 7,933,652.

(60) Provisional application No. 60/885,428, filed on Jan. 18, 2007.

(51) Int. Cl.
*A61N 1/36* (2006.01)

(52) U.S. Cl. .......................... 607/37; 607/27
(58) Field of Classification Search ...................... 607/27
See application file for complete search history.

(56) References Cited

U.S. PATENT DOCUMENTS

| | | | |
|---|---|---|---|
| 4,236,525 A | 12/1980 | Sluetz et al. | |
| 5,383,913 A | 1/1995 | Schiff | |
| 5,522,856 A | 6/1996 | Reineman | |
| 5,843,141 A * | 12/1998 | Bischoff et al. | 607/37 |
| 5,897,577 A | 4/1999 | Cinbis | |
| 6,154,675 A * | 11/2000 | Juran et al. | 607/29 |
| 6,317,633 B1 | 11/2001 | Jorgenson | |
| 6,816,745 B1 | 11/2004 | Brand | |
| 6,847,845 B2 | 1/2005 | Belden | |
| 6,895,276 B2 | 5/2005 | Kast | |
| 6,934,588 B1 | 8/2005 | Brand | |
| 6,968,235 B2 | 11/2005 | Belden et al. | |
| 7,286,882 B2 | 10/2007 | Cole | |
| 7,711,427 B2 | 5/2010 | Janzig | |
| 7,711,428 B2 | 5/2010 | Janzig | |
| 7,720,538 B2 | 5/2010 | Janzig | |
| 7,853,332 B2 | 12/2010 | Olsen | |
| 2004/0073266 A1 | 4/2004 | Haefner et al. | |
| 2004/0215240 A1 * | 10/2004 | Lovett et al. | 607/4 |
| 2004/0267328 A1 | 12/2004 | Duffin | |

FOREIGN PATENT DOCUMENTS

| | | |
|---|---|---|
| EP | 1438985 | 1/2004 |
| EP | 1618923 | 1/2006 |
| WO | WO98/48896 | 11/1998 |
| WO | WO00/24459 | 5/2000 |

OTHER PUBLICATIONS

EP07760701.8: Examination Report dated Mar. 12, 2010.

* cited by examiner

*Primary Examiner* — Carl H Layno
*Assistant Examiner* — Jeremiah Kimball (57) ABSTRACT

An implantable signal generator including electronic circuitry, a computer readable medium, and a connector block with a lumen which receives at least one lead. The at least one lead has at least one electrode connector while the lumen of the connector block has a plurality of contacts operably coupled to the electronic circuitry. The computer readable medium contains instructions for carrying out a process to determine at least one piece of information regarding the at least one lead within the lumen based on an electrode connector being electrically connected with the at least one of the plurality of contacts, and an electrode connector not being electrically connected with the at least one of the plurality of contacts.

18 Claims, 3 Drawing Sheets

BI-DIRECTIONAL CONNECTOR ASSEMBLY FOR AN IMPLANTABLE MEDICAL DEVICE

This application is a continuation of Ser. No. 11/735,553, filed Apr. 16, 2007, now U.S. Pat. No. 7,933,652, which claims the benefit of priority to U.S. Provisional Application No. 60/885,428, entitled "BI-DIRECTIONAL CONNECTOR ASSEMBLY FOR AN IMPLANTABLE MEDICAL DEVICE" filed on Jan. 18, 2007, the disclosure of both of which are incorporated herein by reference.

FIELD

The present disclosure relates to a connector for an implantable medical device and particularly to an implantable medical device that can determine information regarding components connected thereto.

BACKGROUND

The medical device industry produces a wide variety of electronic and mechanical devices for treating medical conditions. Commonly used neurostimulators include an implantable signal generator and at least one lead. Different clinicians can choose to implant different leads in the same or different types of patients. Often, one particular neurostimulator can only be used with one particular lead or set of leads. This can require medical device manufacturers to maintain a number of different models of neurostimulators, for example. Production of numerous models of neurostimulators can make manufacturing more expensive, and can cause implant facilities to maintain a larger inventory. Advantages in manufacturing cost and efficiency as well as concomitant reductions in inventory would both be served by allowing different lead configurations to be used with one neurostimulator. Implantable signal generators that can identify the particular leads that are utilized therewith could also be advantageous.

BRIEF SUMMARY

Disclosed is an implantable signal generator that includes a housing; a connector block having a first surface and a second surface; electronic circuitry contained within the housing; a power source contained within the housing; a lumen extending through the connector block from the first surface to the second surface, wherein the lumen is configured to receive at least one lead, wherein said lead includes at least one electrode connector; a plurality of contacts within the lumen, wherein the plurality of contacts are operably coupled to the electronic circuitry; and a computer readable medium containing instructions for carrying out a process to determine at least one piece of information regarding a lead that is received within the lumen, the process including the steps of: measuring at least one characteristic of at least one of the plurality of contacts; and determining which of two ranges the measured characteristic fits, wherein the two ranges of characteristics correspond to an electrode connector being electrically coupled with the at least one of the plurality of contacts, and an electrode connector not being electrically coupled with the at least one of the plurality of contacts; and wherein the range which the measured characteristic fits is used in determining the at least one piece of information regarding the lead.

Also disclosed is an implantable signal generator including a housing; a connector block having a first surface and a second surface; electronic circuitry contained within the housing; a power source contained within the housing; a lumen extending through the connector block from the first surface to the second surface, wherein the lumen is configured to receive at least one lead; and a plurality of contacts housed within the lumen, wherein the plurality of contacts are operably coupled to the electronic circuitry, wherein each of the plurality of contacts are configured to allow electrical connection with at least one electrode connector of at least one lead when the at least one lead is received in the lumen, wherein at least one of the plurality of contacts is not electrically coupled with an electrode connector when the at least one lead can be received in the lumen of the implantable signal generator, and wherein the electrical circuitry is configured to detect the at least one of the plurality of contacts that is not electrically connected with an electrode connector of a lead in order to determine at least one piece of information regarding the at least one lead that can be received in the lumen of the implantable signal generator.

Further disclosed is a system that includes (i) an implantable signal generator that includes a housing; a connector block having a first surface and a second surface; a lumen extending through the connector block from the first surface to the second surface; and a plurality of contacts housed within the lumen; (ii) electronic circuitry that is operably coupled to the implantable signal generator; (iii) a power source that is operably coupled to the implantable signal generator; and (iv) at least one lead that includes at least one electrode; at least one electrode connector; and at least one electrode conductor that electrically connects the at least one electrode and the at least one electrode connector; wherein the connector block is operably coupled with the housing, wherein the plurality of contacts are operably coupled with the electronic circuitry, wherein each of the plurality of contacts are configured to allow electrical connection with one of the at least one electrode connectors when the at least one lead is received in the lumen, wherein at least one of the plurality of contacts is not electrically connected with an electrode connector when the at least one lead is received in the lumen, and wherein the electrical circuitry is configured to detect the at least one of the plurality of contacts that is not electrically connected with an electrode connector in order to determine one piece of information regarding the at least one lead that is received in the lumen Also disclosed is a process for determining at least one piece of information regarding a lead, wherein the lead comprises at least one electrode connector, wherein the lead is received within a lumen, wherein the lumen extends through a connector block of an implantable signal generator from a first surface to a second surface of the connector block, wherein the lumen is configured to receive the at least one lead, wherein the lumen houses a plurality of contacts, wherein the plurality of contacts are operably coupled to electronic circuitry of the implantable signal generator; the process including the steps of: a) measuring at least one characteristic of at least one of the plurality of contacts; and b) determining whether the measured characteristic is within a first range, or a second range, wherein the first range is characteristic of the at least one electrode connector being connected to the at least one contact, and the second range is characteristic of the at least one electrode connector not being connected to the at least one contact, wherein whether the characteristic is within the first range or the second range provides at least one piece of information regarding the at least one lead.

BRIEF DESCRIPTION OF THE DRAWINGS

This disclosure may be more completely understood in consideration of the following detailed description of various embodiments of the disclosure in connection with the accompanying drawings, in which.

The figures provided herein are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawings that form a part hereof, and in which are shown by way of illustration several specific embodiments. It is to be understood that other embodiments are contemplated and are part of this disclosure. The following detailed description, therefore, is not to be taken in a limiting sense.

All scientific and technical terms used herein have meanings commonly used in the art unless otherwise specified. The definitions provided herein are to facilitate understanding of certain terms used herein and are not meant to limit the scope of the disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "implantable medical device" includes, for example, an implantable signal generator (ISG), a cardiac pacemaker, an implantable defibrillator, a congestive heart failure device, a hearing implant, a cochlear implant, a neurostimulator, a drug pump, a ventricular assist device, an insulin pump, an implantable sensing system, an artificial heart, a bone growth stimulator, or a prosthetic device, and the like.

Examples of "operably coupled" include, but are not limited to, electrically coupled, electrically connected, mechanically coupled, mechanically coupled, electrically and mechanically coupled, electrically and mechanically connected, and capable of being operably coupled.

Figure 1:
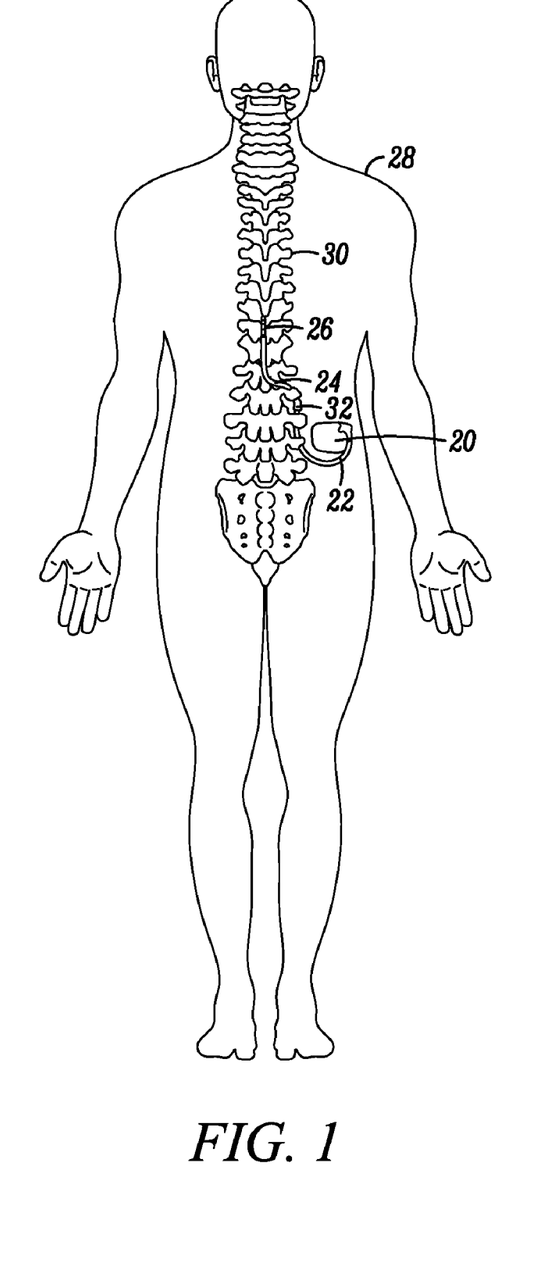
FIG. 1 is a schematic diagram of an active medical device implanted within a human body.

FIG. 1 is a schematic diagram of an implantable medical device 20 implanted within a human body or patient 28. The implantable medical device 20 is illustrated as an implantable signal generator (ISG) however; the implantable medical device 20 may be any implantable medical device as described above and can be placed in any location within a patient or on the surface of a patient's skin.

In one embodiment, the ISG 20 is utilized with a lead extension 22 having a proximal end coupled to the ISG 20, and a lead 24 having a proximal end coupled to a distal end 32 of the lead extension 22; and a distal end of the lead 24 that includes at least one electrode 26. In other embodiments, the lead 24 proximal end is coupled directly to the ISG 20, without using a lead extension 22. When a lead is referred to herein as connecting to an ISG, it will be understood by one of skill in the art that the lead can be connected to the ISG or the lead extension can be connected to the ISG. It will also be understood that portions of this disclosure that refer to components o the lead connecting to the ISG 20 can be referring to components of the lead or components of the lead extension connecting to the ISG 20. The ISG 20 can be implanted in any useful region of the body such as in the abdomen of a patient 28. Similarly, the lead 24 can be implanted at any useful region in the body, such as somewhere along the spinal cord 30. It will also be understood that a lead 24 as referred to herein can be modified to be used with other types of implantable medical devices and still be within the present disclosure.

Figure 2:
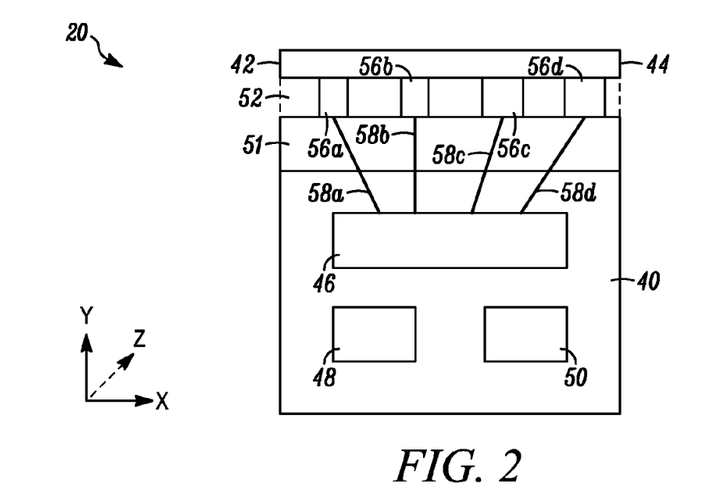
FIG. 2 is a schematic view of an implantable signal generator (ISG)

One embodiment of an ISG 20 is depicted in FIG. 2. The ISG 20 depicted in FIG. 2 includes a housing 40. The housing 40 generally functions to contain at least some of the other components of the ISG 20. In one embodiment, housing 40 can be generally a rectangular type shape that is wider and higher than it is deeper. Another way of demonstrating this, with respect to FIG. 2 is that the depth of the device in the z direction (into the paper) is less than the width in the x direction or the height in the y direction. The ISG 20 is operably coupled to the electronic circuitry 46 that generally functions to control the ISG 20. In one embodiment, the electronic circuitry is housed within the housing 40 of the ISG 20. In another embodiment, the electronic circuitry 46 is not contained within the housing 40, but is still operably coupled to the ISG 20. The ISG 20 is also operably coupled to a power source 48. The power source 48 can be contained within the housing 40 or can be outside the housing 40, but still be operably coupled to the ISG 20. The power source 48 can be a battery or an inductive coil, or other components known to those of skill in the art. In one embodiment, the ISG 20 is also operably coupled to memory 50. In one embodiment, the memory 50 is contained within the housing 40, and in another embodiment, the memory 50 is outside the housing 40 but is still operably coupled to the ISG 20.

The ISG 20 also includes an operably coupled connector block 51. The connector block 51 can be an item that is separate from the ISG 20 but is permanently or releasably attached to the housing 40, or the connector block 51 can be integral with the housing 40 and can be a designated portion of the housing 40. The connector block 51 includes a lumen 52 that extends through the connector block 51 from one surface of the connector block 51 to another surface of the connector block 51. In one embodiment, the lumen 52 extends through the connector block 51 from the first surface 42 to the second surface 44. The lumen 52 is generally configured to receive at least a portion of a lead within at least a portion of the lumen 52. The lumen 52 can also be configured to receive more than one lead. In one embodiment, the lumen 52 is configured to receive two leads or one lead. The lumen 52 houses at least one contact 56. In one embodiment, the lumen 52 houses a plurality of contacts 56a, 56b, 56c, and 56d. The plurality of contacts 56 are operably coupled to the electronic circuitry 46, as exemplified by lines 58a, 58b, 58c, and 58d.

Figure 3:
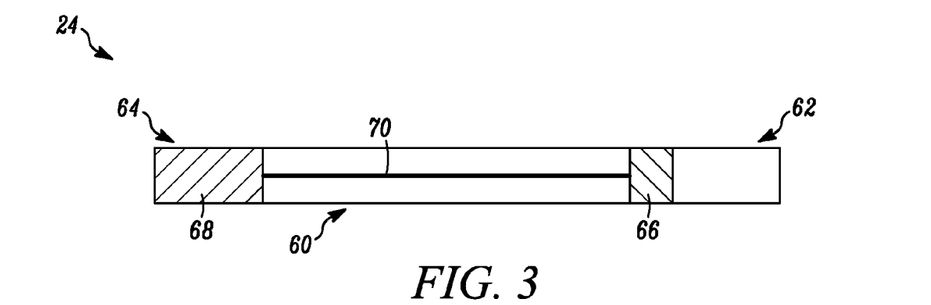
FIG. 3 is a schematic view of a portion of a lead.

FIG. 3 depicts an exemplary lead 24 that can be utilized with an ISG 20 as described herein. In one embodiment, a lead 24 has a lead body 60, which has a lead distal end 62 and a lead proximal end 64. The lead 24 also includes at least one electrode 66. In one embodiment, a lead 24 having at least four electrodes is utilized. In another embodiment, a lead having at least eight electrodes is utilized. One of skill in the art will understand, having read this specification, that any types of electrodes normally utilized can be utilized herein. Examples of such electrodes include, but are not limited to, ring electrodes, coil electrodes, and segmented electrodes. A lead 24 that can be utilized herein also includes at least one electrode connector 68. The electrode connector 68 functions to electrically connect the lead 24, and more specifically, the at least one electrode 66 of the lead 24 with the at least one contact 56 of the connector block 51. The lead 24 also includes at least one electrode conductor 70 that functions to electrically connect the at least one electrode 66 to the at least one electrode connector 68.

In one embodiment, the lead 24 includes a wire having insulation thereon and includes one or more insulated electrical conductors each coupled at their proximal end to a connector and to contacts or electrodes 26 at its distal end. Some leads are designed to be inserted into a patient percutaneously (e.g. the Model 3487A Pisces-Quad® lead available from Medtronic, Inc.), and some are designed to be surgically implanted (e.g. Model 3998 Specify® lead, also available form Medtronic, Inc.). In some embodiments, the lead 24 may contain a paddle at its distal end for housing electrodes 66. In many embodiments, electrodes 66 may include one or more ring contacts at the distal end of lead 24.

As discussed above, it will also be understood by one of skill in the art that a lead extension 22 can be utilized herein. When a lead extension 22 is utilized, the lead extension 22 will interact with the connector block 51 instead of the lead 24 interacting with the connector block 51. For example, the lead extension 22 will be electrically connected to the lead 24, and the lead extension 22 will house the electrical connection that ultimately electrically connects the electrode 66 with the contact(s) 56 in the connector block 51.

The ISG 20 and one or more leads can be utilized with a system. Such a system may also include a physician programmer and a patient programmer (not shown). In one embodiment, the ISG 20 can include an implantable signal generator of the type available from Medtronic, Inc., which is generally capable of generating multiple pulses occurring either simultaneously or one pulse shifting in time with respect to the other, and having independently varying amplitudes and pulse widths. The ISG 20 is operably coupled to a power source and the electronics for sending precise, electrical pulses to the patient to provide a desired treatment or therapy. While the ISG 20, in many embodiments, provides electrical stimulation by way of pulses, other forms of stimulation may be used such as continuous electrical stimulation.

The housing 40 and the connector block 51 can be made of any material commonly known to those of skill in the art, including but not limited to titanium, and other such metals. In one embodiment, the material that makes up the housing and the connector block are a biocompatible material. Exemplary materials include those that are utilized in implantable signal generators available from Medtronic, Inc (Minneapolis, Minn.). It will also be understood by one of skill in the art that possible configurations and dimensions of the housing 40 of the ISG 20 are generally known and can generally be utilized. Exemplary configurations and materials include those that are utilized in implantable signal generators available from Medtronic, Inc (Minneapolis, Minn.). One embodiment of an ISG 20 that can be utilized has a housing 40 and a connector block 51 that are integrally formed. In such an embodiment, the connector block is a separate portion of the housing that houses the lumen. The connector block 51 and housing 40 can be made of the same type of material, can be made from the same piece of material, or can be made of separate materials and can be mechanically joined together. In some embodiments, the connector block is a separate piece that is joined to the housing. In some embodiments, the connector block is a portion of the housing and is only distinguished by being the portion of the housing 40 that contains the lumen 52. Commonly owned U.S. application Ser. No. 11/733,240 entitled "INTERNAL HERMETIC LEAD CONNECTOR FOR IMPLANTABLE DEVICE" by Gerald Lindner, Chris Paidosh, and Darren Janzig, filed on Apr. 10, 2007 (now U.S. Pat. No. 7,711,427, issued May 4, 2010), the disclosure of which is incorporated herein by reference, exemplifies an embodiment wherein the connector block is a portion of the housing and is only distinguished by being the portion of the housing 40 that contains the lumen 52.

The electronic circuitry 46 that is operably coupled with the ISG 20 can generally be similar to those known to one of skill in the art. Examples of such can be found in implantable signal generators available from Medtronic, Inc. (Minneapolis, Minn.). The power source 48 of the ISG 20 can also generally be similar to that known to those of skill in the art. Examples of such can be found in implantable signal generators available from Medtronic, Inc. (Minneapolis, Minn.). The memory 50 can generally include any magnetic, electronic, or optical media, such as random access memory (RAM), read-only memory (ROM), electronically-erasable programmable ROM (EEPROM), flash memory, or the like, or a combination thereof. Examples of such can be found in implantable signal generators available from Medtronic, Inc.

The lumen 52 extends through the connector block 51 from the first surface 42 to the second surface 44. The lumen 52 is configured to receive at least one lead. The configuration of the lumen 52 is at least somewhat based on the configuration of a lead 24 which can be received within the lumen 52. The lumen 52 allows for bidirectional entry of one lead. By bidirectional entry, it is meant that a lead can enter from either surface of the connector block 51. This can be advantageous because it can allow for a more natural placement of the ISG 20 within a subcutaneous pocket that is created for it within a patient 28. It can also allow the lead 24 or the lead extension 22 to more easily be wrapped around the ISG 20 when it is implanted in a patient 28. In one embodiment, the lumen 52 has substantially the same average diameter throughout its length. Such a lumen could have repeating diameter changes for example, that ultimately render the lumen having substantially the same average diameter throughout. Such a lumen can be distinguished from one that has a constriction within it for example.

The lumen 52 houses at least one contact 56. The at least one contact 56 functions to operably couple, or more specifically, at least electrically couple the lead 24 or lead extension 22 to the ISG 20. The at least one contact 56 can be part of a larger structure within the lumen 52, or can be one of a plurality of structures within the lumen (the other structures can including further contacts as well as different structures). In one embodiment, the lumen can include at least one contact as well as at least one other structure that can function to secure a lead within the lumen. In another embodiment, the lumen can include at least one contact as well as at least one other structure that can function to electrically isolate one lead from another. Some of the at least one contact and other structures, if present, may be joined together to form a larger structure that is housed within the lumen.

Figure 4:
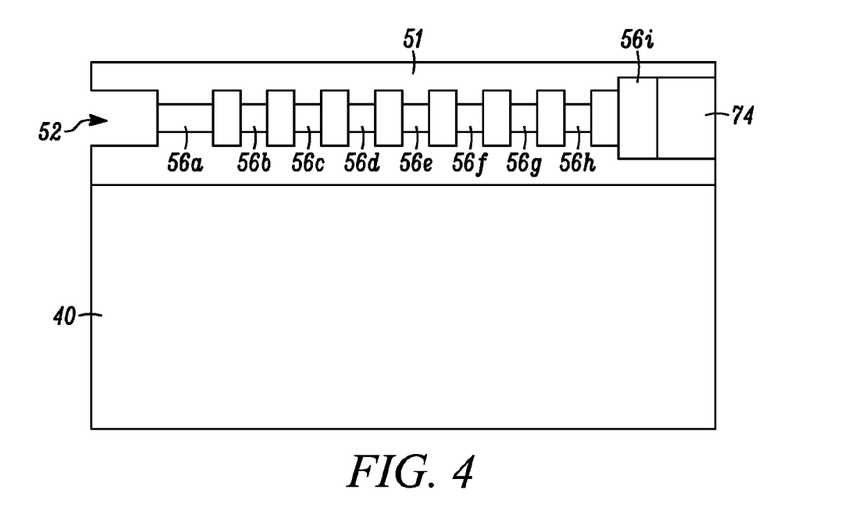
FIG. 4 is a diagram of an illustrative ISG.

The lumen 52 houses at least one contact 56 that is or can be operably connected to the electronic circuitry 46. In one embodiment, the lumen 52 houses a plurality of contacts 56a, 56b, 56c, and 56d, for example. In one embodiment, a lumen 52 houses nine (9) contacts 56. Such an embodiment is depicted in FIG. 4. This figure illustrates the housing 40, the connector block 51, the lumen 52, and the contacts 56a, 56b, 56c, 56d, 56e, 56f, 56g, 56h, and 56i. It should also be understood that an ISG 20 or more specifically, a connector block 51 can include more than one lumen 52 that houses at least one contact.

The contacts 56 can include material configured to provide electrical contact. In one embodiment, the contact can also mechanically stabilize the lead and/or the electrode connector that the contact is in contact with. Materials and configurations that can be utilized as contacts 56 are known to those of skill in the art. Examples of such configurations include, but are not limited to set screws made of an electrically conductive material, coil springs that can make electrical contact, friction fit contacts (also referred to as wiping contacts or beam contacts), or similar devices. A specific example of a coil spring that can make an electrical contact is a Bal Seal contact ring available from Bal Seal Engineering Co. Inc (Foothill Ranch, Calif.). Other examples of such devices can be found in implantable signal generators available from Medtronic, Inc. (Minneapolis, Minn.) for example. In one embodiment, a combination of more than one type of contact can be housed in the lumen 52. In one embodiment, both set screws and coil springs that make electrical contact can be utilized housed in one lumen 52. The exemplary embodiment depicted in FIG. 4 shows a lumen 52 that houses both set screws and coil springs, such as Bal Seal contact rings. The embodiment depicted therein includes two set screws and seven Bal Seal contact rings. Specifically, in that embodiment, the contacts designated as 56a, and 56i are set screws, and the contacts designated as 56b, 56c, 56d, 56e, 56f, 56g, and 56h are coil springs, such as Bal Seal contact rings. Such an embodiment can provide the advantage of mechanically securing the lead 24 or lead extension 22 in the lumen 52 with the set screws at the ends of the lumen 52, while not adding more time to an implant procedure than is necessary.

One embodiment includes an ISG that contains or is operably coupled to a computer readable medium containing instructions for carrying out a process to determine at least one piece of information regarding a lead that is received within the lumen, the process includes the steps of measuring at least one characteristic of at least one of the plurality of contacts, and determining which of two ranges the measured characteristic fits, wherein the two ranges of characteristics correspond to an electrode connector being electrically connected with the at least one of the plurality of contacts, and an electrode connector not being electrically connected with the at least one of the plurality of contacts.

The instructions are for carrying out a process to determine at least one piece of information regarding a lead that is received within the lumen. The information regarding the lead that can be determined, includes, but is not limited to, the number of electrodes on the lead, the type of electrodes on the lead, the model of the lead, whether the lead includes a sensing electrode as well as a stimulating electrode, which side of the connector block 51 the lead is entering into (first surface 42 or the second surface 44), how many leads are entering the ISG (one or two), and whether the lead is magnetic resonance imaging (MRI) safe or not MRI safe. In one embodiment, the process determines the number of electrodes on the lead and how many leads are entering the connector block 51. Other information regarding the lead can also be determined using a process as described herein.

Figure 5:
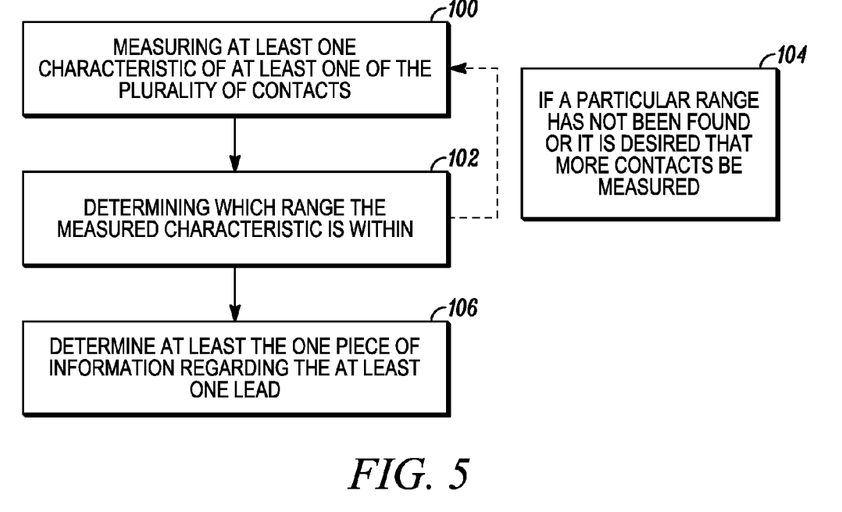
FIG. 5 is a diagram illustrating a process of determining at least one piece of information regarding at least one lead.

The process can also be carried out in other fashions, i.e., the instructions do not need to be housed in memory on the ISG 20. The steps of the process are illustrated in FIG. 5. As seen therein, the process includes a step 100 of measuring at least one characteristic of at least one of the plurality of contacts. Exemplary characteristics that can be measured include, but are not limited to, impedance, and potential across the contacts. In an embodiment where impedance is measured, commercially available leads can be utilized without modification because many commercially available leads are already configured to check impedance.

The process also includes a step 102 of determining which range the measured characteristic is within. For example, in an embodiment where impedance is the characteristic that is being measured, checking the impedance of one of the contacts will either return an impedance value that is characteristic of an electrode connector being connected thereto, or a value that is characteristic of an electrode connector not being connected thereto. An impedance value that is indicative of an electrode connector being connected thereto with an inoperable or incorrectly operating electrode could also be returned.

The process can also optionally include the step 104 that measures another characteristic of at least one of the plurality of contacts if a particular range has not been found or if it is desired that more contacts be measured. For example, the impedance of second and further contacts could be measured if the first contact returns a value that is indicative of a lead connector not being present. For example, if a particularly desired value of impedance, has been found, or the impedance of the desired number of contacts have been measured, or some combination thereof, the at least one piece of information regarding the at least one lead can be determined.

The process also includes a step 106 of determining the at least one piece of information regarding the at least one lead. In one embodiment of the process, where impedance is the characteristic that is measured, the information that is to be determined is the number of leads connected to the ISG, the number of electrodes on the leads, and the direction which the lead is entering the ISG. Table 1 below provides an example of possible measured characteristics and the information that can be determined in this embodiment. The particular configuration that this table refers to is the exemplary embodiment depicted in FIG. 4. As discussed previously, the embodiment depicted in FIG. 4 includes nine contacts, designated as 56a, 56b, 56c, 56d, 56e, 56f, 56g, 56h, and 56i respectively.

TABLE 1

| The contact whose impedance measurement is within a range that dictates it is open (i.e. not in contact with an electrode connector) | Lead configuration |
| --- | --- |
| Contact 56a | One lead having 8 electrodes entering the lumen of the ISG from the second surface 44 |
| Contact 56i | One lead having 8 electrodes entering the lumen of the ISG from the first surface 42 |
| Contact 56e | Two leads both having 4 electrodes entering from both the first surface 42 and the second surface 44 |
| Contact 56a, 56b, 56c, 56d, and 56e | One lead having 4 electrodes entering the lumen of the ISG from the second surface 44 |

TABLE 1-continued

| The contact whose impedance measurement is within a range that dictates it is open (i.e. not in contact with an electrode connector) | Lead configuration |
|---|---|
| Contact 56e, 56f, 56g, 56h, and 56i | One lead having 4 electrodes entering the lumen of the ISG from the first surface 42 |

In one embodiment, the at least one piece of information regarding the lead that is received within the lumen can be transmitted to another component. In one embodiment, the information can be transmitted to another component, such as a programmer, for example, a physician programmer, a patient programmer, or both. In one embodiment, the transmitted information can be displayed on the physician programmer, the patient programmer, or both (not shown). In another embodiment, the at least one piece of information regarding the lead that is received within the lumen can be transmitted to a programmer and be utilized in the programming of the device. For example, during programming of some implantable signal generators, the physician inputs information into the physician programmer, patient programmer, or both in order to set up the therapy program; in this embodiment, the at least one piece of information regarding the lead that is received within the lumen can be determined using a method disclosed herein, and automatically input into the physician programmer, patient programmer, or both. This could allow the programming process to become easier, more efficient, or easier to be accomplished by a less skilled clinician. In another embodiment, the at least one piece of information can be used to check the accuracy of information that was input into a programmer, by a physician for example, during programming.

Another embodiment includes an implantable signal generator that includes a housing, a connector block having a first surface and a second surface, electronic circuitry that is operably coupled to the ISG, a power source that is operably coupled to the ISG, a lumen extending through the connector block 51 from the first surface to the second surface, wherein the lumen is configured to receive at least one lead, and a plurality of contacts housed within the lumen, wherein the plurality of contacts are operably coupled to the electronic circuitry wherein each of the plurality of contacts are configured to allow electrical connection with at least one electrode connector of at least one lead when the at least one lead is received in the lumen, wherein at least one of the plurality of contacts is not electrically connected with an electrode connector when the at least one lead is received in the lumen, and wherein the electronic circuitry is configured to detect the at least one of the plurality of contacts that is not electrically connected with an electrode connector of a lead in order to determine at least one piece of information regarding the at least one lead that can be received in the lumen. In one embodiment, the electronic circuitry and the power source are contained within the housing.

In such an embodiment, each of the plurality of contacts is configured to be operably coupled to the electronic circuitry as well as with one electrode connector from a lead or a lead extension. As discussed above, the contacts can include, but are not limited to, devices which are known to those of skill in the art, including coil springs that afford electrical connections (such as Bal Seals), set screws, and friction fit contacts. Utilization of such devices for the contacts as well as electrical connection with the electrode connector would be well within the level of one of ordinary skill in the art.

In such an embodiment, a lead (or leads) that is (are) received in the lumen 52 will, because of the configuration of the contact within the lumen and the lead or leads, always have at least one contact that is not electrically connected with an electrode connector. As used herein, a contact that is not electrically connected is one that, even though at least one lead is received in the lumen and operably coupled to the ISG via the at least one contact, is not electrically connected, or in physical contact with an electrode connector. The particular one of the plurality of contacts that is not electrically connected with an electrode connector can be determined using a process as described above. The particular contact that is not electrically connected with an electrode connector can then be utilized to determine at least one piece of information regarding the lead or leads.

Another embodiment includes a system that includes (i) an implantable signal generator that includes a housing, a connector block having a first surface and a second surface, a lumen extending through the connector block from the first surface to the second surface, and a plurality of contacts within the lumen; (ii) electronic circuitry that is operably coupled to the ISG; (iii) a power source that is operably coupled to the ISG; and (iv) at least one lead that includes at least one electrode, at least one electrode connector, and at least one electrode conductor that electrically connects the at least one electrode and the at least one electrode connector, wherein the connector block is operably coupled to the housing, wherein each of the plurality of contacts are configured to allow electrical connection with one of the at least one electrode connectors when the at least one lead is received in the lumen, wherein at least one of the plurality of contacts is not electrically connected with an electrode connector when the at least one lead is received in the lumen, and wherein the electronic circuitry is configured to detect the at least one of the plurality of contacts that is not electrically connected with an electrode connector in order determine one piece of information regarding the at least one lead that is received in the lumen. In one embodiment, the electronic circuitry and the power source are not contained within the housing, but are located outside the housing and are operably coupled to the ISG.

Figure 6:
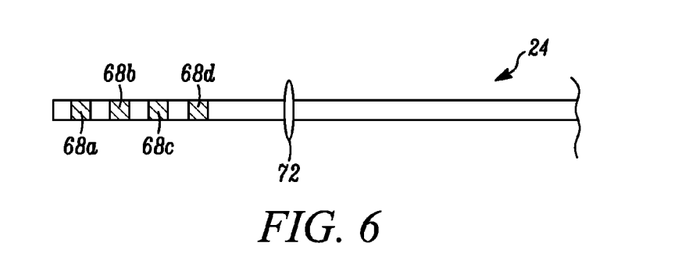
FIG. 6 is a schematic view of a portion of a lead.

In one embodiment, a lead that can be utilized with an ISG as described herein can be modified from that which is normally available and utilized in order to more easily and correctly place the lead 24 within the lumen 52. A depiction of an exemplary lead that has been so modified can be seen in FIG. 6. As seen there, a modified lead can include a flange 72. The flange 72 functions to stop the lead 24 from going too far into the lumen 52. The flange 72 can also be useful in ensuring that the lead goes far enough into the lumen 52 in an embodiment where two leads are inserted into the lumen 52. Such a modification can be useful in leads having any number of electrodes. Because the ISG utilized herein always has an "extra" contact, and the lumen has substantially the same average diameter throughout its length, the leads that are inserted into the lumen can be subject to being advanced too far or not far enough into the connector assembly. Use of a lead 24 with a flange 72 can make the implantation easier and require less time and skill; and or allow easier repositioning of the lead within the lumen. The flange 72 can include any device that would be known to one of skill in the art for fulfilling this purpose. Examples of such devices include ferrules, or the like.

Figure 7:
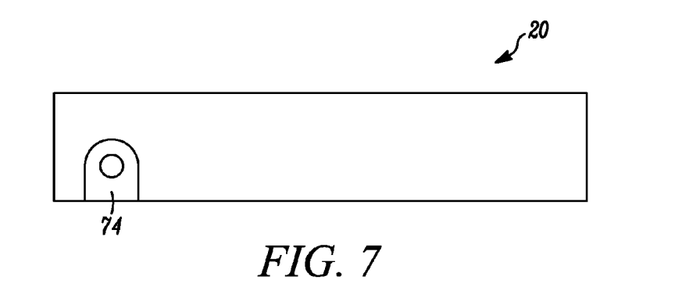
FIG. 7 is a diagram of the second surface of the ISG depicted in FIG. 4.

The ISGs that are utilized herein can also be used in combination with a sealing plug 74 which can be utilized in situations where only one lead is used. An example of a sealing plug 74 can be seen in FIGS. 4 and 7. The sealing plug 74 functions to seal the lumen 52 from the environment outside the ISG. This can be advantageous because bodily fluids won't be able to come into contact with the connector assembly once the ISG is implanted into the body of a patient.

What is claimed is:

1. An implantable signal generator comprising:
a housing;
a connector block having a first surface and a second surface; electronic circuitry contained within the housing;
a power source contained within the housing;
a lumen extending through the connector block from the first surface to the second surface, wherein the lumen has a length from the first surface to the second surface, wherein the lumen is configured to receive at least one lead, wherein said lead comprises at least one electrode connector;
a plurality of contacts within the lumen, wherein the plurality of contacts are operably coupled to the electronic circuitry; and
a non-transitory computer readable medium containing instructions for carrying out a process to determine at least one piece of information regarding a lead that is received within the lumen, the process comprising the steps of:
measuring at least one characteristic of at least one of the plurality of contacts; and
determining which of two ranges the measured characteristic fits, wherein the two ranges of characteristics correspond to an electrode connector being electrically coupled with the at least one of the plurality of contacts, and an electrode connector not being electrically coupled with the at least one of the plurality of contacts; and wherein the range which the measured characteristic fits is used in determining the at least one piece of information regarding the lead.

2. The implantable signal generator according to claim 1, wherein the lumen has substantially the same average diameter throughout its length.

3. The implantable signal generator according to claim 1, wherein the housing and the connector block are two separate pieces that are operably coupled together.

4. The implantable signal generator according to claim 1, wherein the plurality of contacts comprises both coil springs and set screws.

5. The implantable signal generator according to claim 1, wherein the plurality of contacts comprises seven coil springs and two set screws.

6. The implantable signal generator according to claim 5, wherein the two set screws are closest respectively to the first and second surfaces of the connector block.

7. The implantable signal generator according to claim 1, wherein the computer readable medium comprises random access memory (RAM), read-only memory (ROM), electronically-erasable programmable ROM (EEPROM), or flash memory.

8. The implantable signal generator according to claim 1, wherein the at least one characteristic that is measured is impedance.

9. The implantable signal generator according to claim 1, wherein the process further comprises measuring at least one characteristic of each of the plurality of contacts.

10. The implantable signal generator according to claim 1, wherein the process further comprises transmitting the information regarding the at least one lead to a programmer.

11. The implantable signal generator according to claim 10, wherein the process further comprises utilizing the transmitted information in programming the implantable signal generator.

12. An implantable signal generator comprising:
a housing;
a connector block having a first surface and a second surface;
electronic circuitry contained within the housing;
a power source contained within the housing;
a lumen extending through the connector block from the first surface to the second surface, wherein the lumen is configured to receive at least one lead; and
a plurality of contacts housed within the lumen, wherein the plurality of contacts are operably coupled to the electronic circuitry,
wherein each of the plurality of contacts are configured to allow electrical connection with at least one electrode connector of at least one lead when the at least one lead is received in the lumen,
wherein at least one of the plurality of contacts is not electrically coupled with an electrode connector when the at least one lead can be received in the lumen of the implantable signal generator, and
wherein the electrical circuitry is configured to detect the at least one of the plurality of contacts that is not electrically connected with an electrode connector of a lead in order to determine at least one piece of information regarding the at least one lead that can be received in the lumen of the implantable signal generator.

13. A process for determining at least one piece of information regarding a lead,
wherein the lead comprises at least one electrode connector,
wherein the lead is received within a lumen,
wherein the lumen extends through a connector block of an implantable signal generator from a first surface to a second surface of the connector block,
wherein the lumen is configured to receive the at least one lead,
wherein the lumen houses a plurality of contacts,
wherein the plurality of contacts are operably coupled to electronic circuitry of the implantable signal generator;
the process comprising the steps of:
a) measuring at least one characteristic of at least one of the plurality of contacts; and
b) determining whether the measured characteristic is within a first range, or a second range, wherein the first range is characteristic of the at least one electrode connector being connected to the at least one contact, and the second range is characteristic of the at least one electrode connector not being connected to the at least one contact,
wherein whether the characteristic is within the first range or the second range provides at least one piece of information regarding the at least one lead.

14. The process according to claim 13, wherein the at least one characteristic is impedance.

15. The process according to claim 13, wherein the at least one piece of information is chosen from the group consisting of the number of electrodes on the lead, the type of electrodes on the lead, whether the lead includes a sensing electrode, which side of the connector block the lead is entering into, how many leads are entering the connector block, whether the lead is MRI safe or not MRI safe, and combinations thereof.

16. The process according to claim 13 further comprising measuring at least one characteristic of a second contact.

17. The process according to claim 13 further comprising transmitting the at least one piece of information regarding the lead into a programmer.

18. The process according to claim 17, wherein the process further comprises utilizing the transmitted information in programming the implantable signal generator.

* * * * *